United States Patent
Ries et al.

(10) Patent No.: US 10,189,776 B2
(45) Date of Patent: Jan. 29, 2019

(54) STEREOSELECTIVE PROCESS

(71) Applicant: Boehringer Ingelheim International GmbH, Ingelheim am Rhein (DE)

(72) Inventors: Uwe Joerg Ries, Birerach an der Riss (DE); Nizar Haddad, Danbury, CT (US); Bo Qu, Brookfield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/758,446

(22) PCT Filed: Sep. 16, 2016

(86) PCT No.: PCT/EP2016/072019
§ 371 (c)(1),
(2) Date: Mar. 8, 2018

(87) PCT Pub. No.: WO2017/046355
PCT Pub. Date: Mar. 23, 2017

(65) Prior Publication Data
US 2018/0258031 A1 Sep. 13, 2018

Related U.S. Application Data

(60) Provisional application No. 62/220,434, filed on Sep. 18, 2015.

(51) Int. Cl.
| | |
|---|---|
| C07C 269/06 | (2006.01) |
| C07F 9/6571 | (2006.01) |
| C07D 307/58 | (2006.01) |
| C07C 315/04 | (2006.01) |
| B01J 31/02 | (2006.01) |

(52) U.S. Cl.
CPC ......... *C07C 269/06* (2013.01); *B01J 31/0258* (2013.01); *C07C 315/04* (2013.01); *C07D 307/58* (2013.01); *C07F 9/6571* (2013.01); *B01J 2231/34* (2013.01); *C07B 2200/07* (2013.01); *C07C 2601/10* (2017.05); *C07C 2601/16* (2017.05)

(58) Field of Classification Search
CPC .................................................. C07C 269/06
USPC .......................................................... 549/321
See application file for complete search history.

(56) References Cited

U.S. PATENT DOCUMENTS

| | | |
|---|---|---|
| 2014/0221335 A1 | 8/2014 | Gnamm et al. |
| 2014/0249129 A1 | 9/2014 | Gnamm et al. |
| 2016/0060230 A1 | 3/2016 | Gnamm et al. |
| 2016/0060231 A1 | 3/2016 | Gnamm et al. |
| 2016/0340319 A1 | 11/2016 | Gnamm et al. |

FOREIGN PATENT DOCUMENTS

| | | |
|---|---|---|
| WO | 2014122160 A1 | 8/2014 |
| WO | 2014135414 A1 | 9/2014 |

OTHER PUBLICATIONS

Akiyama et al., Chiral Bronsted acid-catalyzed hydrophosphonylation of imines-DFT study on the effect of substituents of phosphoric acid 11, Tetrahedron, Elsevier Science Publishers, 2009, vol. 65, No. 26, pp. 4950-4956.
International Search Report and Written Opinion for corresponding application PCT/EP2016/072019, dated Jan. 13, 2017.

*Primary Examiner* — Taofiq A Solola
(74) *Attorney, Agent, or Firm* — Philip I. Datlow

(57) ABSTRACT

The invention relates to a method for the stereoselective preparation of compounds of formula (IV).

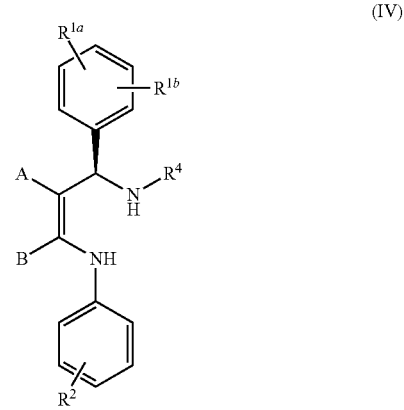

9 Claims, No Drawings

STEREOSELECTIVE PROCESS

BACKGROUND OF THE INVENTION

Technical Field

The invention relates to a method for the stereoselective preparation of compounds of formula (IV)

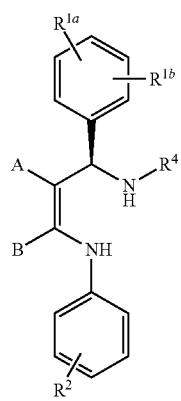

(IV)

BACKGROUND INFORMATION

WO2014/122160 describes substituted bicyclic dihydropyrimidinones and their use as inhibitors of neutrophil elastase activity. Intermediates described therein are of the type of formula (IV). Single enantiomers of compounds described therein are obtained by preparative chromatography on a chiral phase.

The problem of the present invention is to provide a stereoselective process for preparing compounds of formula (IV).

DESCRIPTION OF THE INVENTION

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, S(O), $S(O)_2$, NC (cyano), HOOC, $F_3C$ or the like, the skilled artisan can see the radical attachment point(s) to the molecule from the free valences of the group itself. For combined groups comprising two or more subgroups, the first or last named subgroup, where the free valence is indicated, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk or a broken line may be used in sub-formulas to indicate the bond which is connected to the core molecule as defined.

For example, the term "3-carboxypropyl-group" represents the following substituent:

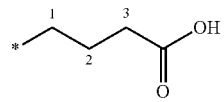

wherein the carboxy group is attached to the third carbon atom of the propyl group. The terms "1-methylpropyl-", "2,2-dimethylpropyl-" or "cyclopropylmethyl-" group represent the following groups:

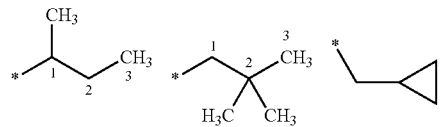

The asterisk may be used in sub-formulas to indicate the bond which is connected to the core molecule as defined.

Many of the following terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

All isomeric forms (especially all stereoisomeric forms, e.g. all chiral, enantiomeric, diastereomeric and racemic forms, all tautomeric and all geometric isomeric forms) of a compound of the present invention are intended with this invention, unless the specific isomer is specifically indicated. Obviously, the isomer which is pharmacologically more potent and/or more efficacious is preferred.

It will be appreciated that the compounds of the present invention contain at least one asymmetrically substituted carbon atom, and may therefore be isolated as pure enantiomers or as a racemic or non-racemic mixture of both enantiomers. It will be appreciated that some of the compounds of the present invention contain more than one stereogenic center, that is more than one asymmetrically substituted carbon or sulfur atom, and may therefore be isolated as pure diastereomers or as diastereomeric mixtures, both in optically active or racemic forms.

The invention contemplates all conceivable stereoisomers, particularly the diastereomers and enantiomers mentioned herein, e.g. in substantially pure form, in enriched form (e.g. substantially free of any or all other undesired enantiomers and/or diastereomers and/or in any mixing ratio, including the racemic forms, as well as the salts thereof.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

As used herein, "salts" refer to derivatives of the disclosed compounds wherein the parent compound is modified by making acid or base salts thereof. Examples of salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

DETAILED DESCRIPTION OF THE INVENTION

The present invention solves the problem stated above by means of the method of synthesis described hereinafter.

The invention relates to a method for the stereoselective preparation of compounds of formula (IV), see scheme 1,

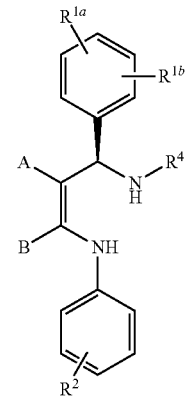

(IV)

wherein $R^{1a}$ is NC—;

$R^{1b}$ is H, $CH_3S$—, Br, or $CH_3SO_2$—;

A is NC—;

B is $CH_3$;

or A and B together with the carbon atoms to which they are attached form a ring selected from the group consisting of cyclopentenone, cyclohexenone and furanone;

$R^2$ is $F_3C$—;

$R^4$ is

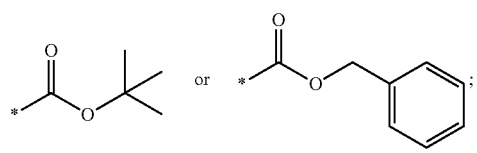

characterised in that the method comprises step (C), where step (C) is the stereoselective reaction of a compound of formula (I)

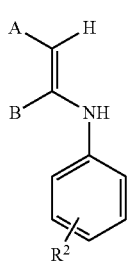

(I)

with a compound of formula (III)

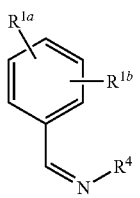

(III)

wherein A, B, $R^{1a}$, $R^{1b}$, $R^2$ and $R^4$ have the meanings as defined above;
in the presence of an organo-catalyst of formula (X)

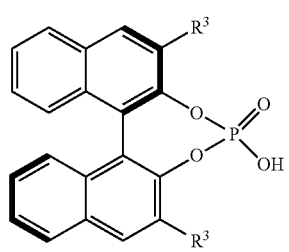

(X)

wherein
$R^3$ is selected from the group consisting of

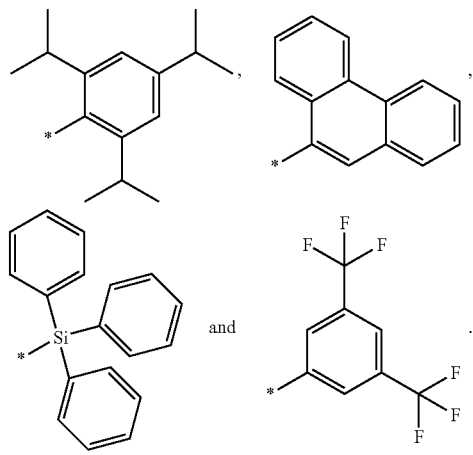

Another embodiment of the invention relates to the above method, see scheme 1, for the preparation of compounds of formula (IV-A)

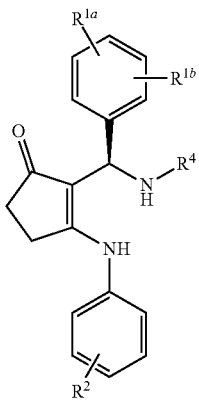

(IV-A)

wherein a compound of formula (I-A)

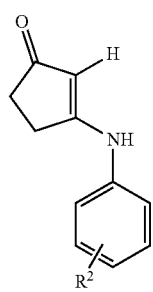

(I-A)

is reacted with a compound of formula (III) in the presence of an organo-catalyst of formula (X);
wherein $R^{1a}$, $R^{1b}$ $R^2$, $R^3$ and $R^4$ have the meanings as defined above.

Another embodiment of the invention relates to the above method, see scheme 1, wherein $R^4$ of formula (IV) is

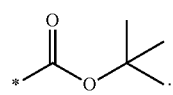

Another embodiment of the invention relates to the above method, see scheme 1, wherein $R^3$ of the organo-catalyst of formula (X) is

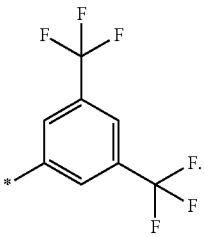 [SMILES: *c1cc(C(F)(F)F)cc(C(F)(F)F)c1]

Another embodiment of the invention relates to the above method, see scheme 1, wherein step (C) is carried out at a temperature from 0° C. to −70° C.
Another embodiment of the invention relates to the above method, see scheme 1, wherein step (C) is carried out at a temperature from −20° C. to −70° C.

Another embodiment of the invention relates to the above method, see scheme 1, wherein step (C) is carried out at a temperature from −50° C. to −60° C.

Another embodiment of the invention relates to the above method, see scheme 1, wherein step (C) is carried out in a solvent selected from the group consisting of ethyl acetate, Me-THF, THF, dichloromethane, isopropyl acetate, n-butyl acetate, toluene and DMF.

Another embodiment of the invention relates to the above method, see scheme 1, wherein step (C) is carried out in a solvent selected from the group consisting of ethyl acetate, Me-THF, THF, dichloromethane and toluene.

Another embodiment of the invention relates to the above method, see scheme 1, wherein step (C) is carried out in a solvent selected from the group consisting of ethyl acetate, Me-THF, THF and dichloromethane.

Another embodiment of the invention relates to the above method, see scheme 1, wherein step (C) is carried out using from 0.3 mol % to 10 mol % of the organo-catalyst of formula (X).

Another embodiment of the invention relates to the above method, see scheme 1, wherein step (C) is carried out using from 0.5 mol % to 5 mol % of the organo-catalyst of formula (X).

Another embodiment of the invention relates to the above method, see scheme 1, wherein step (C) is carried out using from 0.6 mol % to 1 mol % of the organo-catalyst of formula (X).

Another embodiment of the invention relates to the above method, see scheme 1, wherein step (C) is carried out using from 1.0 to 1.5 molar equivalents of the compound of formula (I).

Another embodiment of the invention relates to the above method, see scheme 1, wherein step (C) is carried out using from 1.0 to 1.2 molar equivalents of the compound of formula (I).

Another embodiment of the invention relates to the above method, see scheme 1, wherein step (C) is carried out using 1.1 molar equivalents of the compound of formula (I).

Another embodiment of the invention relates to the above method, see scheme 1, wherein step (C) is carried out using 1.0. molar equivalents of the compound of formula (III).

Another embodiment of the invention relates to the above method, see scheme 1, wherein step (C) is preceded by step (B) wherein the compound of formula (II)

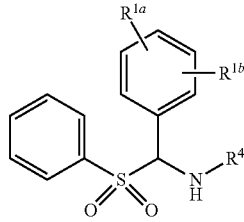

(II)

is reacted with an inorganic salt to give the compound of formula (III)

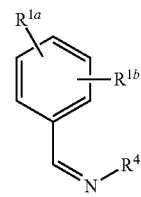

(III)

wherein $R^{1a}$, $R^1$ and $R^4$ have the meanings as defined above.

Another embodiment of the invention relates to the above method, see scheme 1, wherein step (B) is carried out at a temperature from 20 to 120° C.

Another embodiment of the invention relates to the above method, see scheme 1, wherein step (B) is carried out at a temperature from 20 to 80° C.

Another embodiment of the invention relates to the above method, see scheme 1, wherein step (B) is carried out at a temperature from 25 to 60° C.

Another embodiment of the invention relates to the above method, see scheme 1, wherein step (B) is carried out using inorganic salts selected from the group consisting of $Na_2SO_4$, $K_2CO_3$, $Na_2CO_3$, $Cs_2CO_3$, CsF, KF and $K_3PO_4$.

Another embodiment of the invention relates to the above method, see scheme 1, wherein step (B) is carried out using inorganic salts selected from the group consisting of $Na_2SO_4$, $K_2CO_3$, $Na_2CO_3$ and $Cs_2CO_3$.

Another embodiment of the invention relates to the above method, see scheme 1, wherein step (B) is carried out using inorganic salts selected from the group consisting of $Na_2SO_4$ and $K_2CO_3$.

Another embodiment of the invention relates to the above method, see scheme 1, wherein step (B) is carried out in water and an organic solvent selected from the group consisting of dichloromethane, THF, Me-THF, ethyl acetate, isopropyl acetate, n-butyl acetate and toluene.

Another embodiment of the invention relates to the above method, see scheme 1, wherein step (B) is carried out in water and an organic solvent selected from the group consisting of dichloromethane, THF, Me-THF and ethyl acetate.

Another embodiment of the invention relates to the above method, see scheme 1, wherein step (B) is preceded by step (A') wherein the compound of formula (I)

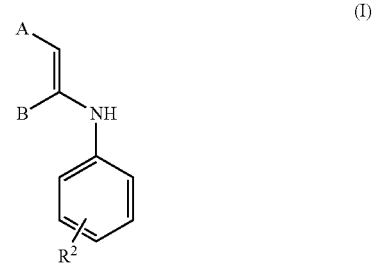

(I)

is prepared by reacting a substituted aniline of formula (I')

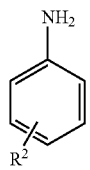
(I')

with a compound of formula (I")

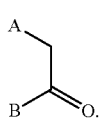
(I")

Another embodiment of the invention relates to the above method, see scheme 1, wherein step (A') is carried out at a temperature from 25 to 125° C.

Another embodiment of the invention relates to the above method, see scheme 1, wherein step (A') is carried out at a temperature from 50 to 120° C.

Another embodiment of the invention relates to the above method, see scheme 1, wherein step (A') is carried out at a temperature from 70 to 100° C.

Another embodiment of the invention relates to the above method, see scheme 1, wherein step (A') is carried out in a solvent selected from the group consisting of toluene, ethyl acetate, isopropyl acetate, n-butyl acetate and dioxane.

Another embodiment of the invention relates to the above method, see scheme 1, wherein step (A') is carried out in a solvent selected from the group consisting of toluene, isopropyl acetate and n-butyl acetate.

Another embodiment of the invention relates to the above method, see scheme 1, wherein step (A') is carried out in a solvent selected from the group consisting of toluene and isopropyl acetate.

Another embodiment of the invention relates to the use of a compound of formula (IV) above, for the manufacture of substituted bicyclic dihydropyrimidinones for use as inhibitors of neutrophil elastase activity.

Another embodiment of the invention relates to a compound of formula (IV) above, for the manufacture of substituted bicyclic dihydropyrimidinones for use as inhibitors of neutrophil elastase activity.

Each and any of the above definitions for steps (A'), (B) and (C) may be combined with each other.

Another embodiment of the invention relates to a method for the preparation of organo-catalyst of formula (X), see scheme 2

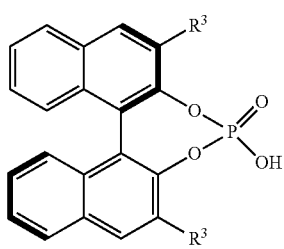
(X)

wherein $R^3$ is

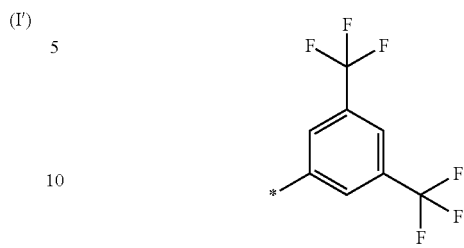

characterised in that the method comprises a Suzuki-Miyaura coupling of unprotected 3,3'-dibromo-1,1-bi-2-napthol with 3,5-bis-(trifluoromethyl)phenyl boronic acid in the presence of palladium diacetate and a ligand of formula (Y)

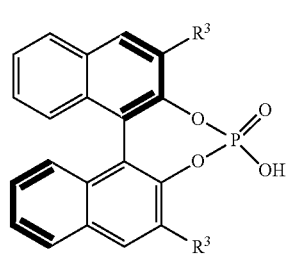
(Y)

Another embodiment of the invention relates to a method for the preparation of an organo-catalyst of formula (X), see scheme 2

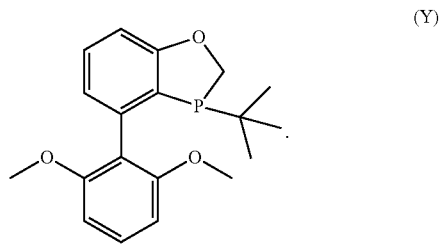 [SMILES: COc1cccc(OC)c1-c1cccc2c1P(C(C)(C)C)CO2]
(X)

wherein $R^3$ is

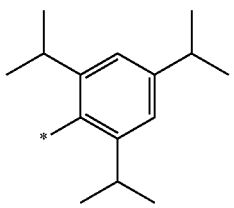 [SMILES: *c1c(C(C)C)cc(C(C)C)cc1C(C)C]

characterised in that the method comprises a Suzuki-Miyaura coupling of unprotected 3,3"-dibromo-1,1-bi-2-napthol with 3,5-bis-(trifluoromethyl)phenyl boronic acid in the presence of palladium diacetate and a ligand of formula (Y)

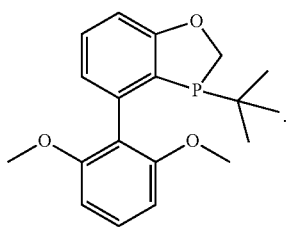

(Y)

Another embodiment of the invention relates to a method for the preparation of organo-catalyst of formula (X), see scheme 2

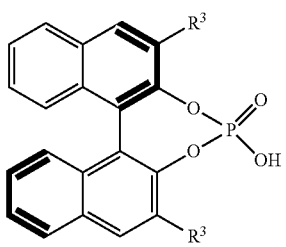

(X)

wherein R³ is

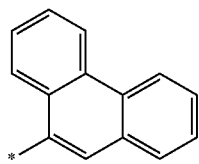 [SMILES: *c1cc2ccccc2c2ccccc12]

characterised in that the method comprises a Suzuki-Miyaura coupling of unprotected 3,3'-dibromo-1,1-bi-2-napthol with 3,5-bis-(trifluoromethyl)phenyl boronic acid in the presence of palladium diacetate and a ligand of formula (Y)

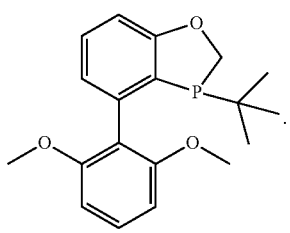

(Y)

Another embodiment of the invention relates to a method for the preparation of organo-catalyst of formula (X), see scheme 2

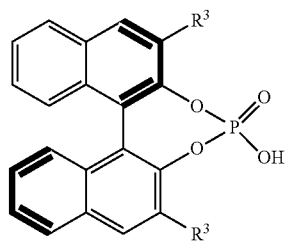

(X)

wherein R³ is

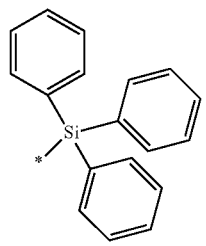 [SMILES: *[Si](c1ccccc1)(c1ccccc1)c1ccccc1]

characterised in that the method comprises a Suzuki-Miyaura coupling of unprotected 3,3'-dibromo-1,1-bi-2-napthol with 3,5-bis-(trifluoromethyl)phenyl boronic acid in the presence of palladium diacetate and a ligand of formula (Y)

(Y)

Preparation

Starting materials are commercially available or may be prepared by methods that are described in the literature or herein, or may be prepared in an analogous or similar manner.

Any functional groups in the starting materials or intermediates may be protected using conventional protecting groups. These protecting groups may be cleaved again at a suitable stage within the reaction sequence using methods familiar to the one skilled in the art.

The following abbreviations are used in the experimental section:
THF—Tetrahydrofuran
DMF—Dimethylformamide
Me-THF—2-Methyl-tetrahydrofuran
HPLC—High performance liquid chromatography
ee—Enantiomer excess
ESI—Electrospray ionization
MS—Mass spectroscopy
CAS—Chemical abstract service
NMR—Nuclear magnetic resonance spectroscopy
MPLC—Medium pressure liquid chromatography
HCl—Hydrochloric acid The synthesis according to the invention is illustrated in schemes 1 and 2.

Scheme 1: Synthesis of compounds of formula (IV) wherein A, B, $R^{1a}$, $R^{1b}$, $R^2$ and $R^4$ are given the meanings as defined above.

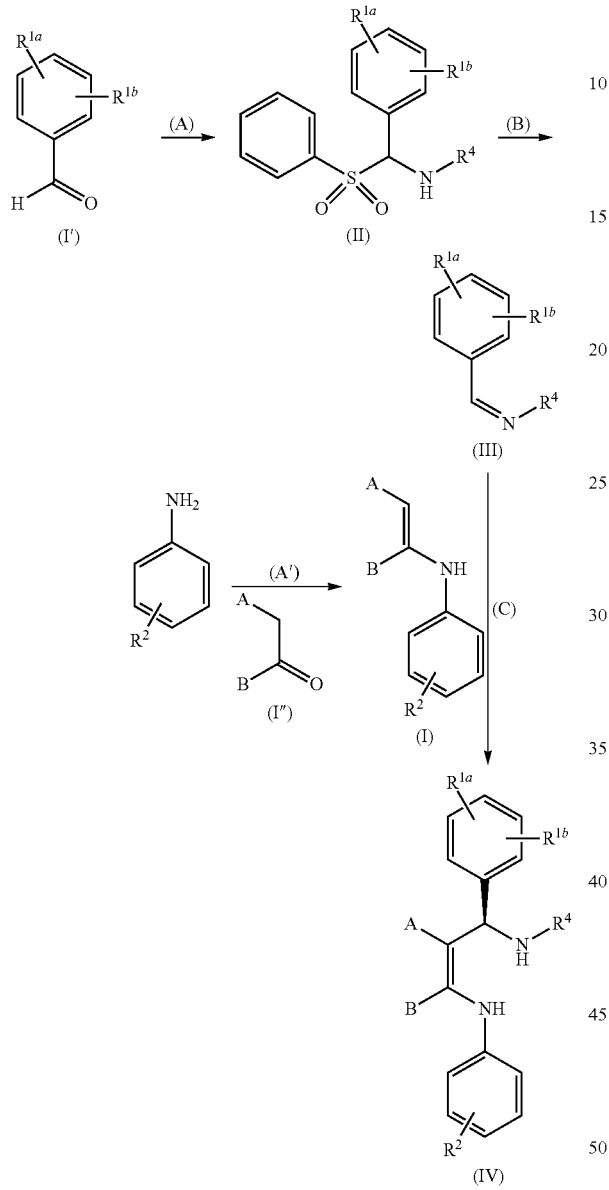

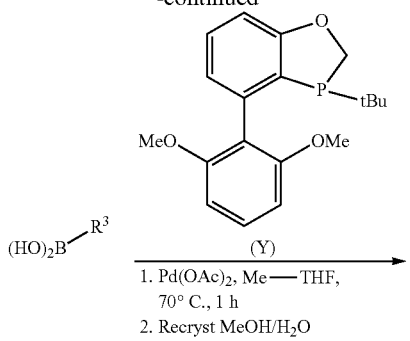

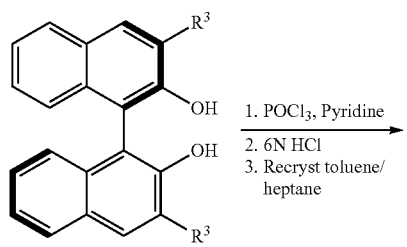

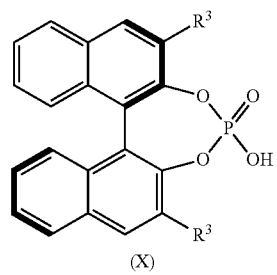

EXAMPLES

Example 1

Carbamic Acid, (R)—N-[(4-cyanophenyl)[5-oxo-2-[[3-(trifluoromethyl)phenyl]amino]-1-cyclopenten-1-yl]methyl]-, 1,1-dimethylethyl ester Scheme 2: Synthesis of organo-catalysts of formula (X), wherein $R^3$ is given the meanings as defined above.

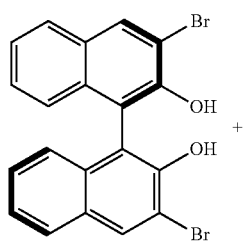

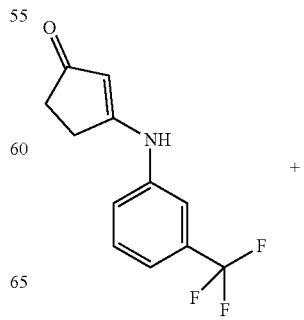

-continued

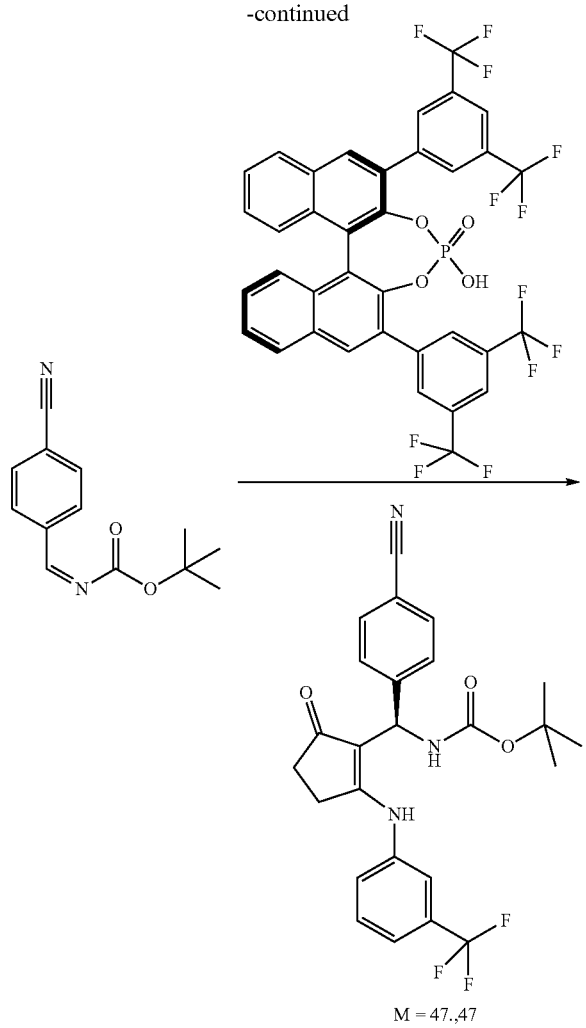

M = 47.,47

At ambient temperature 3-[[3-(trifluoromethyl)phenyl] amino]-2-cyclopenten-1-one (2.45 g, 10.1 mmol) is suspended in 47 ml ethyl acetate. After addition of 196 mg (0.25 mmol) (R)-3,3'-bis[3,5-bis(trifluoromethyl)phenyl]-1,1'-binaphthyl-2,2'-dihydrogen-phosphate the mixture is cooled to −70° C. Subsequently a solution of 3.08 g (12.69 mmol) carbamic acid, N-[(4-cyanophenyl)methylene]-1,1-dimethylethyl ester in 9 ml ethyl acetate is added while the temperature does not exceed −64° C. After 3 hours at −64° C. cooling is removed and the reaction mixture is stirred for 15 hours. HPLC control indicates almost complete reaction without formation of side products. Solvent is removed under vacuum and the residue is dissolved in 4.9 ml of warm ethyl acetate. After addition of 6.5 ml n-heptane the mixture is seeded with the desired product. Subsequently 6.5 ml n-heptane are added. The resulting yellow suspension is stirred 2.5 h at ambient temperature and filtered. The residue is washed with 5 ml ethyl acetate/heptane 3:8 and dried at 50° C.

Yield: 3.58 g (7.59 mmol=75%)
Retention time HPLC (method A): 3.49 min
HPLC purity: 99.4 area %
ee: 93.2% (method B)
ESI-MS: $(M-H)^-=470$, $(M+Na)^+=494$, $(M+H)^+=472$ Example 2

Analogous to example 1 it is possible to perform this reaction using other chiral phosphorous acids instead of (R)-3,3'-bis[3,5-bis(trifluoromethyl)phenyl]-1,1'-binaphthyl 2,2'-dihydrogenphosphate as catalyst.

TABLE 1

Impact of chiral phosphorous acids on yield and enantioselectivity

| Catalyst-Chemical Structure | Catalyst-Chemical Name/CAS-Number | Solvent | Yield (%) | ee (%, method B) |
|---|---|---|---|---|
| | (R)-3,3'-Bis(2,4,6-triisopropylphenyl)-1,1'-binaphthyl-2,2'-diyl-hydrogenphosphate/ 791616-63-2 | Me—THF | 82 | 60 |

TABLE 1-continued

Impact of chiral phosphorous acids on yield and enantioselectivity

| Catalyst-Chemical Structure | Catalyst-Chemical Name/CAS-Number | Solvent | Yield (%) | ee (%, method B) |
|---|---|---|---|---|
| | (R)-3,3'-Bis(9-phenanthryl)-1,1'-binaphthalene-2,2'-diyl-hydrogenphosphate/ 864943-22-6 | Me—THF | 95 | 60 |
| | (R)-(−)-3,3'-Bis(triphenylsilyl)-1,1'-binaphthyl-2,2'-diyl-hydrogenphosphate/ 791616-55-2 | Me—THF | 84 | 30 |

Example 3

Carbamic Acid, (R)—N-[(4-cyano-2-methylthiophenyl)[5-oxo-2-[[3-(trifluoromethyl)phenyl]amino]-1-cyclopenten-1-yl]methyl]-, 1,1-dimethylethyl ester

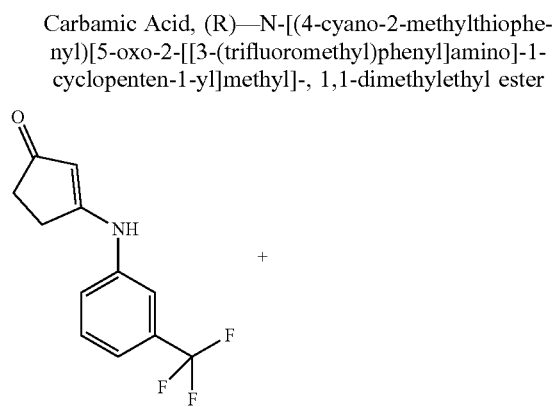

+

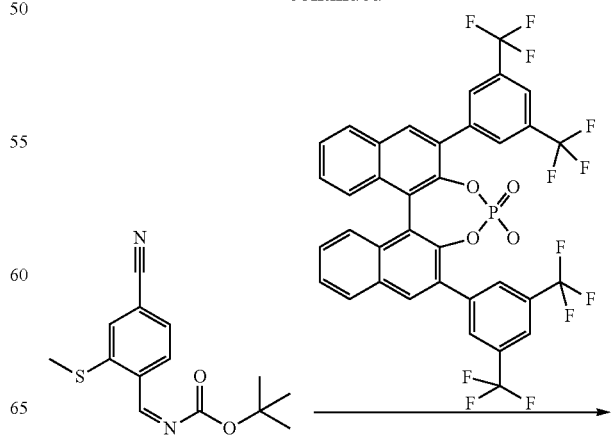

-continued

19
-continued

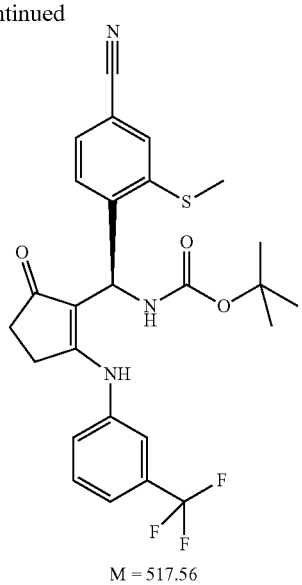

M = 517.56

At ambient temperature 0.2 g (0.83 mmol) 3-[[3-(trifluoromethyl)phenyl]amino]-2-cyclopenten-1-one and 23 mg (0.03 mmol) (R)-3,3'-bis[3,5-bis(trifluoromethyl)phenyl]-1,1'-binaphthyl-2,2'-dihydrogenphosphate are suspended in 5 ml toluene. The mixture is cooled to −41° C. and a solution of 0.296 g (0.91 mmol) carbamic acid, N-[(2-methylthio-4-cyano-phenyl)methylen]-1,1-dimethylethylester in 5 ml toluene is added, while the temperature does not exceed −37° C. After 1 hour at −50° C. the reaction mixture is stirred for 16 h at −33° C. Subsequently the temperature is raised to 8° C. within 6 hours. After 3 days at ambient temperature HPLC indicates incomplete conversion. Solvent is removed under vacuum, a sample of the raw material is dissolved in methanol, water and acetic acid and purified via prep. HPLC.

Yield: n.d.
Retention time HPLC (method C): 5.5 min
ee: 45% (method D)

If this reaction is performed in dichloromethane incomplete conversion is observed. However, ee increases to 65%.

Example 4

Carbamic Acid, (R)—N-[(2-bromo-4-cyanophenyl) [5-oxo-2-[[3-(trifluoromethyl)phenyl]amino]-1-cyclopenten-1-yl]methyl]-, 1,1-dimethylethyl ester

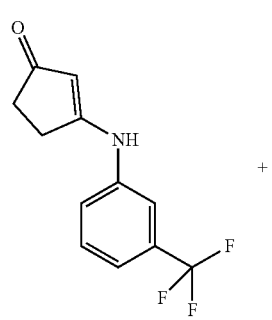

+

20
-continued

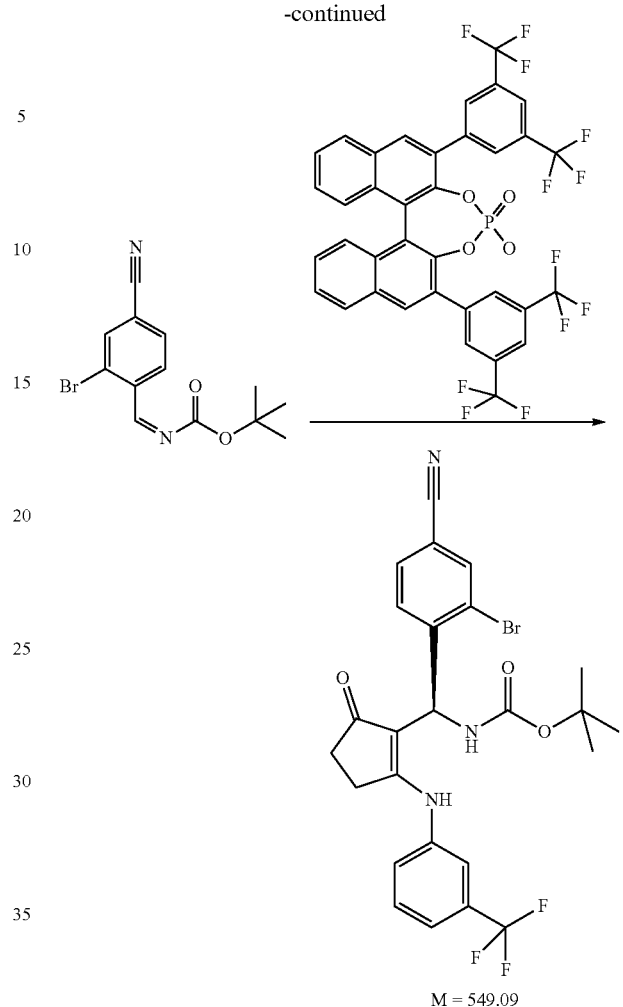

M = 549.09

At ambient temperature 7.5 g (31.1 mmol) 3-[[3-(trifluoromethyl)phenyl]amino]-2-cyclopenten-1-one and 600 mg (0.78 mmol) (R)-3,3'-bis[3,5-bis(trifluormethyl)phenyl]-1,1'-binaphthyl-2,2'-dihydrogenphosphate are suspended in 150 ml ethyl acetate. The mixture is cooled to −75° C. and a solution of 12.4 g (34.2 mmol) carbamic acid, N-[(2-bromo-4-cyanophenyl)methylen]-1,1-dimethylethylester in 50 ml ethyl acetate is added, while the temperature does not exceed −72° C. The reaction mixture is stirred 15 hours while the temperature slowly rises to −20° C. Subsequently the mixture is stirred 1 hour at 0° C. and warmed to ambient temperature. Solvent is removed under vacuum and the residue is purified via MPLC (dichloromethane/methanol 99:1).

Yield: 14.85 g (27 mmol=87%)
Retention time HPLC (method E): 0.74 min
purity (NMR): 90-95%
ee: 98.5% (method F)
ESI-MS: (M−H)⁻=548, (M+H)⁺=550

Example 4.1

At ambient temperature 7.5 g (31.1 mmol) 3-[[3-(trifluoromethyl)phenyl]amino]-2-cyclopenten-1-one and 600 mg (0.78 mmol) (R)-3,3'-bis[3,5-bis(trifluormethyl)phenyl]-1,1'-binaphthyl-2,2'-dihydrogenphosphate are suspended in 150 ml ethyl acetate. The mixture is cooled to −30° C. and a solution of 12.4 g (34.2 mmol) carbamic acid, N-[(2-bromo-4-cyanophenyl)methylen]-1,1-dimethylethylester in 50 ml ethyl acetate is added, while the temperature does not exceed −30° C. The reaction mixture is stirred 15 hours at −30° C. Subsequently the mixture is warmed to ambient temperature. About 90% of the solvent is removed under vacuum and the crystallized solid is isolated by filtration.

Yield: 82-87%, ee=99-100% (Method F).

Example 5

Carbamic Acid, N—[(S)-(2-bromo-4-cyanophenyl) [2,5-dihydro-2-oxo-4-[[3-(trifluoromethyl)phenyl] amino]-3-furanyl]methyl]-, 1,1-dimethylethyl ester

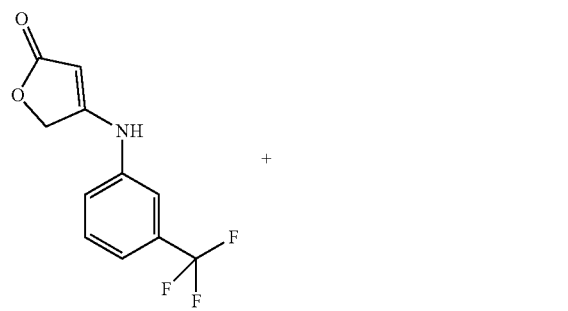

At ambient temperature 8.6 g (35.3 mmol) 4-[[3-(trifluoromethyl)phenyl]amino]-2(5H)-furanone and 682 mg (0.88 mmol) (R)-3,3'-bis[3,5-bis(trifluormethyl)phenyl]-1,1'-binaphthyl-2,2'-dihydrogenphosphate are suspended in 150 ml ethyl acetate. The mixture is cooled to −75° C. and a solution of 14.1 g (38.8 mmol) carbamic acid, N-[(2-bromo-4-cyanophenyl)methylen]-1,1-dimethylethylester in 50 ml ethyl acetate is added, while the temperature does not exceed −72° C. The reaction mixture is stirred 17 hours while the temperature slowly rises to −20° C. Subsequently the mixture is stirred 2 hours at 0° C. and warmed to ambient temperature. Solvent is removed under vacuum and the residue is purified via MPLC (dichloromethane/methanol 99:1).

Yield: 14.85 g (26.9 mmol=76%)

Retention time HPLC (method G): 1.29 min

Purity (NMR): ca. 95% ee: 88% (method H)

ESI-MS: (M−H)⁻=550, (M+H)⁺=552, (M+NH$_4$)⁺=569

Example 6

Carbamic Acid, N—[(S)-(2-bromo-4-cyanophenyl) [6-oxo-2-[[3-(trifluoromethyl)phenyl]amino]-1-cyclohexen-1-yl]methyl]-, 1,1-dimethylethyl ester

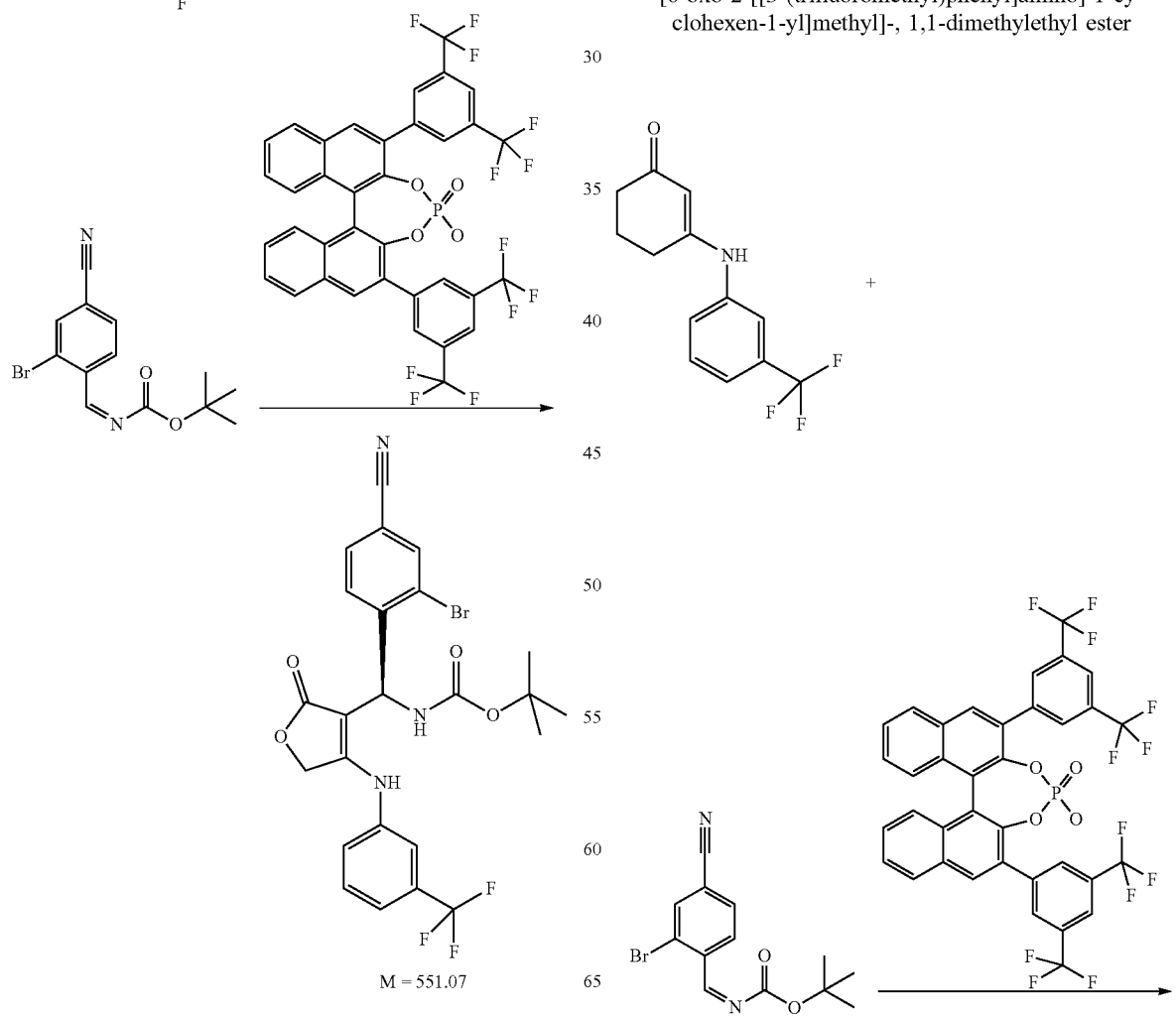

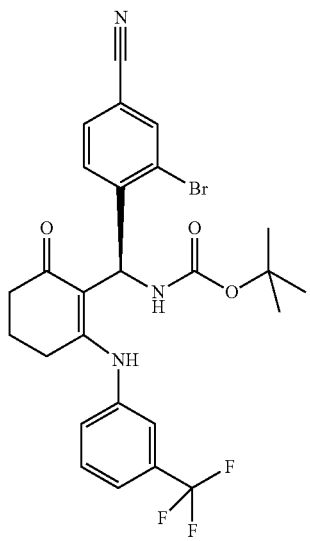

M = 563.10

Synthesis analogous to example 1 using 3-[[3-(trifluoromethyl)phenyl]amino]-2-cyclohexen-1-one (1.31 g=5.13 mmol), carbamic acid, N-[(2-bromo-4-cyanophenyl) methylen]-1,1-dimethylethylester (2.38 g=7.7 mmol) and 97 mg (0.13 mmol) (R)-3,3'-bis[3,5-bis(trifluormethyl)phenyl]-1,1'-binaphthyl-2,2'-dihydrogenphosphate in ethyl acetate at −25 to −34° C.

Yield: 1.12 g (2.0 mmol=39%)

Retention time HPLC (method N): 1.57 min

Purity (NMR): 80-90% ee: 98% (method I)

ESI-MS: (M−H)⁻=562, (M+H)⁺=564

Example 7

Carbamic Acid, N-[(1R,2E)-2-cyano-1-(4-cyanophenyl)-3-[[3-(trifluoromethyl)phenyl]amino]-2-buten-1-yl]-, 1,1-dimethylethyl ester

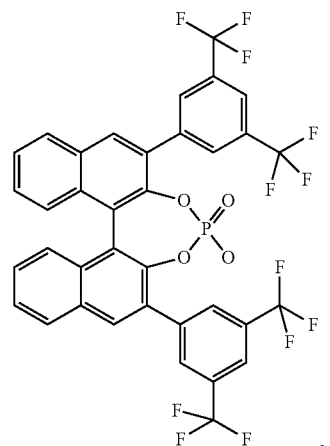

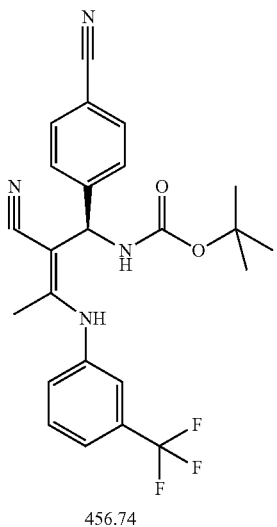

456.74

Synthesis analogous to example 1 using (2E)-3-[[3-(trifluoromethyl)phenyl]amino]-2-butenenitrile (0.5 g=2.21 mmol), carbamic acid, N-[(4-cyanophenyl)methylen]-1,1-dimethylethylester (0.56 g=2.0 mmol) and 17 mg (0.022 mmol) (R)-3,3'-bis[3,5-bis(trifluormethyl)phenyl]-1,1'-binaphthyl-2,2'-dihydrogenphosphate in ethyl acetate at −55 to −53° C. Raw material purified via prep HPLC.

Yield: 0.28 g (0.55 mmol=25%)

Retention time HPLC (method N): 1.56 min

Purity (NMR): 80-90% ee: 87.9% (method K)

ESI-MS: (M−H)⁻=455, (M+H)⁺=457, (M+NH₄)⁺=474

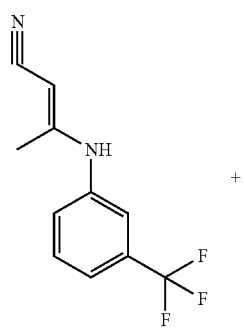

+

Example 8

Carbamic Acid, N-[(1R,2E)-2-cyano-1-(4-cyano-2-methylsulfonylphenyl)-3-[[3-(trifluoromethyl)phenyl]amino]-2-buten-1-yl]-, 1,1-dimethylethyl ester

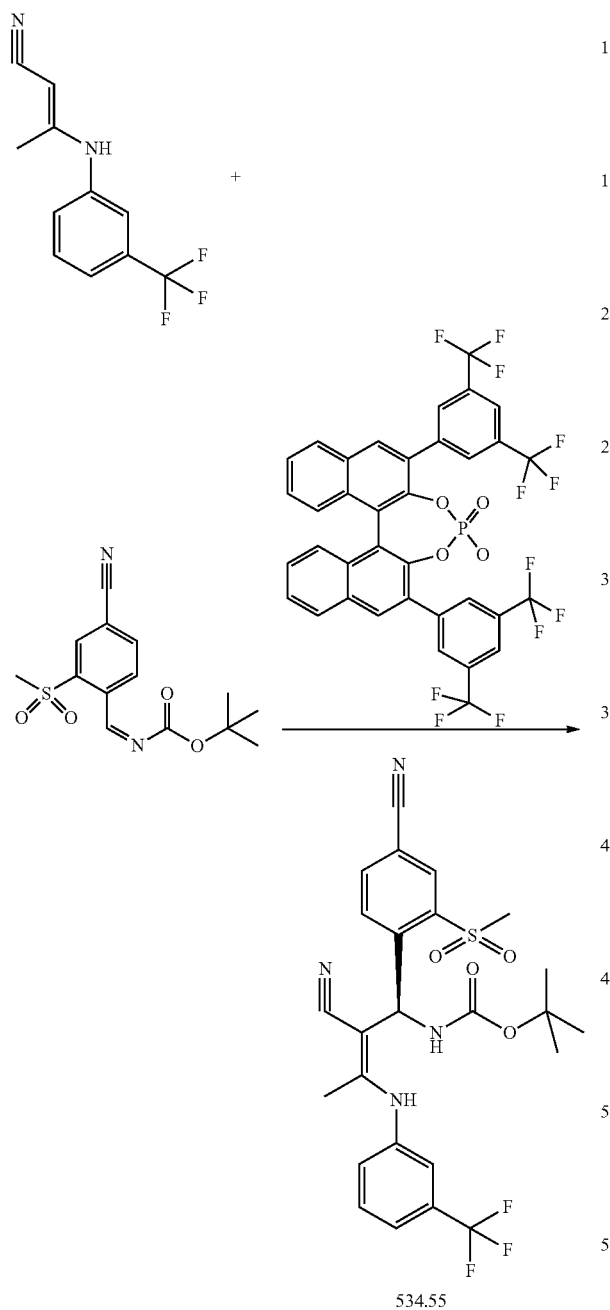

534.55

Synthesis analogous to example 1 using (2E)-3-[[3-(trifluoromethyl)phenyl]amino]-2-butenenitrile (0.5 g=2.21 mmol), carbamic acid, N-[(4-cyano-2-methylsufonylphenyl) methylen]-1,1-dimethylethylester (0.75 g=2.43 mmol) and 17 mg (0.022 mmol) (R)-3,3'-bis[3,5-bis(trifluormethyl) phenyl]-1,1'-binaphthyl-2,2'-dihydrogenphosphate in ethyl acetate at −55 to −53° C. Raw material purified via prep HPLC.

Yield: 0.48 g (0.9 mmol=41%)
Retention time HPLC (method N): 1.49 min
Purity (NMR): 95%
ee: 90.6% (method L)
ESI-MS: (M−H)⁻=533, (M+H)⁺=535, (M+NH₄)⁺=552

Example 9

Carbamic Acid, (R)—N-[(4-cyano-2-methylsulfonylphenyl)[5-oxo-2-[[3-(trifluoromethyl) phenyl]amino]-1-cyclopenten-1-yl]methyl]-, 1,1-dimethylethyl ester

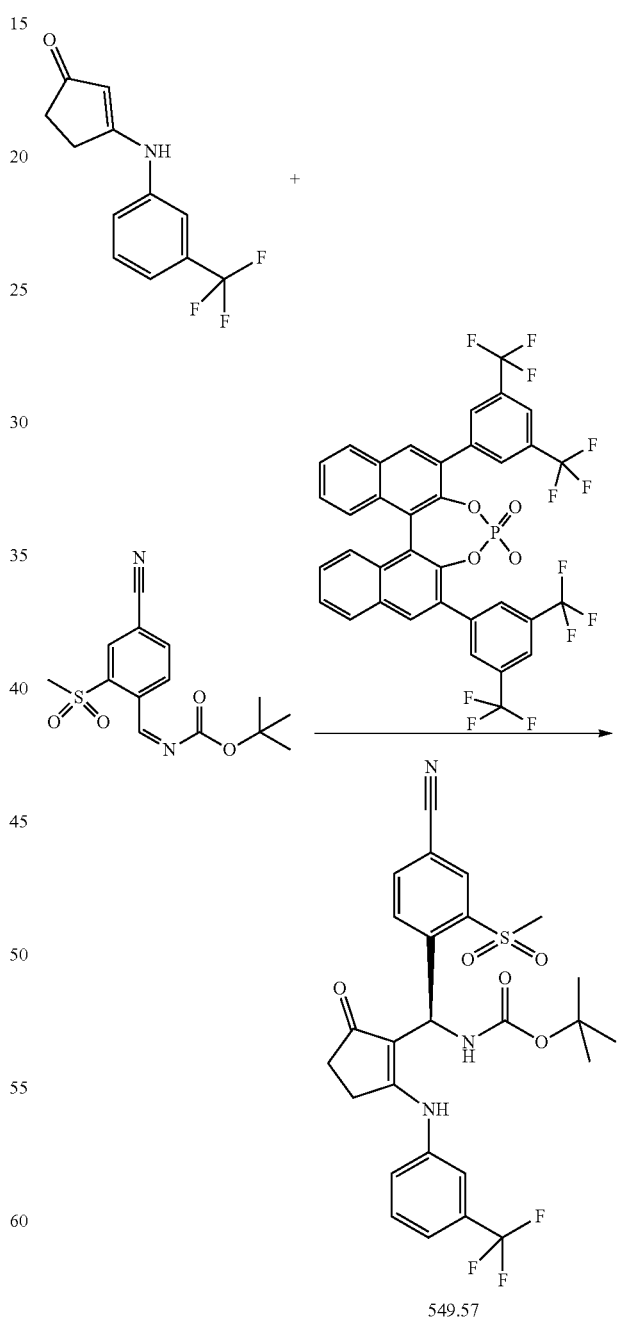

549.57

Synthesis analogous to example 1 using 3-[[3-(trifluoromethyl)phenyl]amino]-2-cyclopenten-1-one (1.3 g=5.24 mmol), carbamic acid, N-[(4-cyano-2-methylsufonylphenyl)methylen]-1,1-dimethylethylester (2.0 g=6.49 mmol) and 96 mg (0.12 mmol) (R)-3,3'-bis[3,5-bis(trifluormethyl)phenyl]-1,1'-binaphthyl-2,2'-dihydrogenphosphate in dichloromethane at −29 to −27° C. Raw material was purified via prep HPLC.

Yield: 2.89 g (4.15 mmol=77%)
Retention time HPLC (method N): 1.54 min
Purity (NMR): 80%
ee: 96.3% (method M)
ESI-MS: (M−H)⁻=548, (M+H)⁺=550
Syntheses of Starting Materials

1. N-[(4-cyanophenyl)methylen]-1,1-dimethylethyl-ester

This compound was synthesized as described by A. S. Tsai et al (*J Am Soc Chem* 133 (May 2011), 1248-50) by reacting tert.butyl carbamate, sodium phenylsulfinate and 4-cyanobenzaldehyde in formic acid/water followed by treatment of the resulting intermediate with potassium carbonate in water/dichloromethane. Analytical data of both compounds corresponded well with literature data.

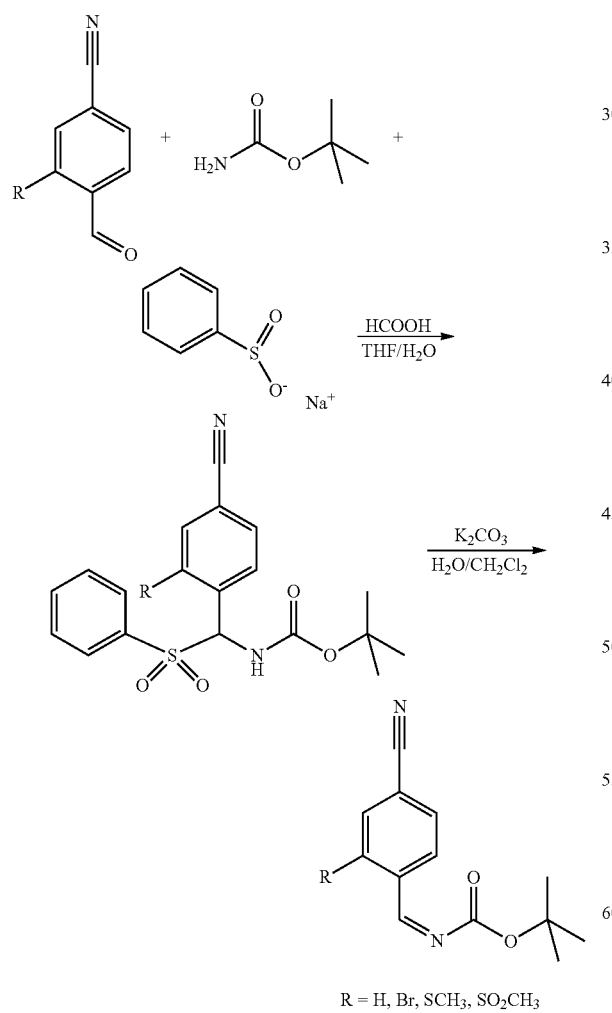

R = H, Br, SCH₃, SO₂CH₃

Carbamic acid, N-[(2-methylthio 4-cyano-phenyl)methylen]-1,1-dimethylethylester, carbamic acid, N-[(2-bromo-4-cyanophenyl)methylen]-1,1-dimethylethylester, carbamic acid, N-[(2-bromo-4-cyanophenyl)methylen]-1,1-dimethylethylester and carbamic acid, N-[(4-cyano-2-methylsufonylphenyl)methylen]-1,1-dimethylethylester were prepared in analogous manner.

2. 3-[[3-(Trifluoromethyl)phenyl]amino]-2-cyclopenten-1-one

This compound was synthesized as described by A. A. Abdelselam et al (*Austr J Chem* 58 (December 2005), 870-6) by reacting cyclopentane-1,3-dione with 3-trifluoromethylaniline. Analytical data corresponded well with literature data.

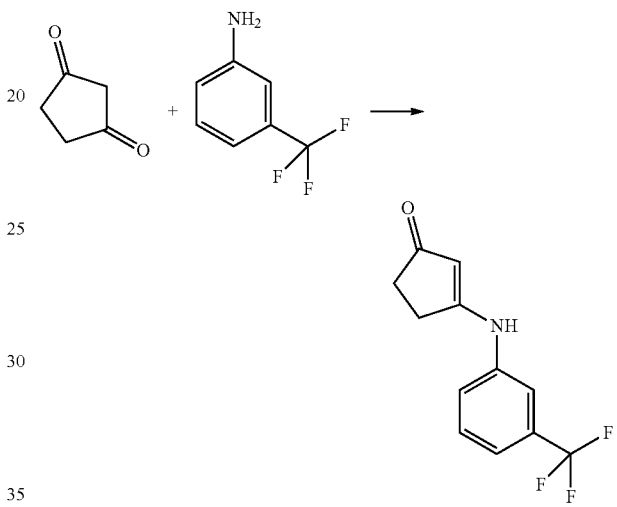

3. 4-[[3-(Trifluoromethyl)phenyl]amino]-2(5H)-furanone

This compound was synthesized as described in WO 2000053581 by reacting 2,4(3H,5H)-furandione with 3-trifluoromethylaniline. Analytical data corresponded well with literature data.

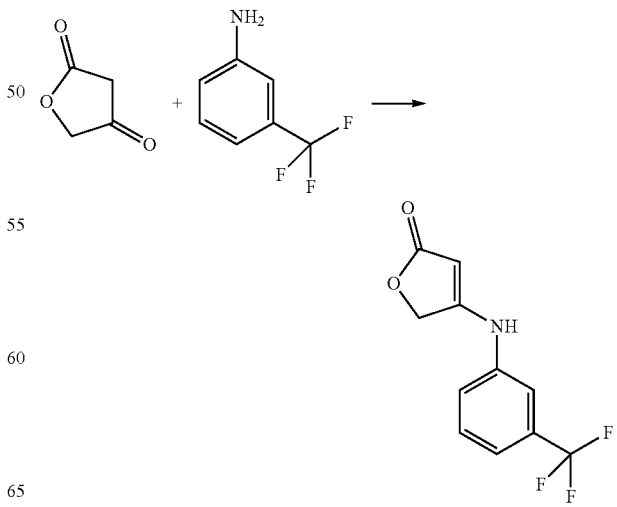

4. 3-[[3-(Trifluoromethyl)phenyl]amino]-2-cyclohexen-1-one

This compound was synthesized as described by A. A. Abdelselam et al (*Austr J Chem* 58 (December 2005), 870-6) by reacting cyclohexane-1,3-dione with 3-trifluoromethylaniline. Analytical data corresponded well with literature data.

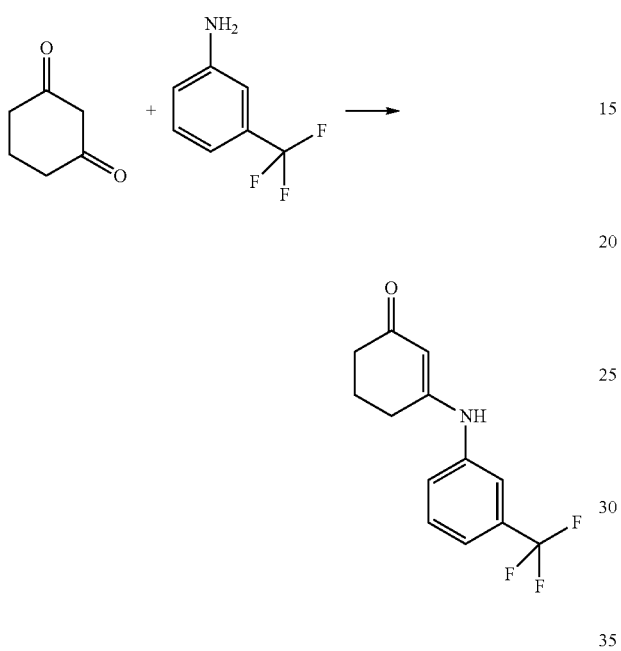

5. (2E)-3-[[3-(trifluoromethyl)phenyl]amino]-2-butenenitrile

This compound was synthesized as described in WO 2004020412 by reacting 3-amino-2-butenenitrile with 3-trifluoromethylaniline. Analytical data corresponded well with literature data.

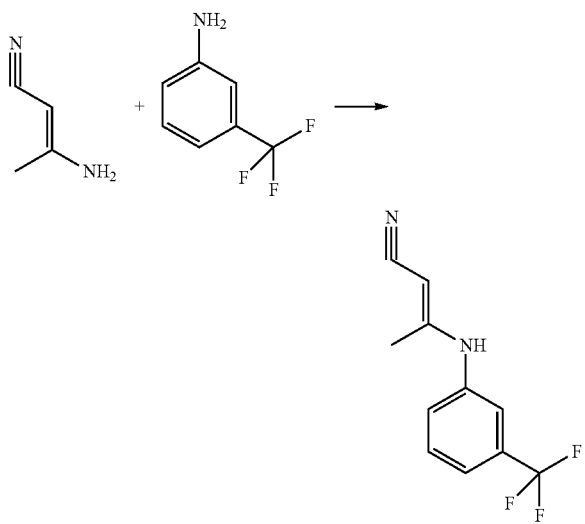

Synthesis of (R)-3,3'-bis[3,5-bis(trifluormethyl)phenyl]-1,1'-binaphthyl-2,2'-dihydrogenphosphate (R)-3,3'-bis(3,5-bis(trifluoromethyl)phenyl)-[1,1'-binaphthalene]-2,2'-diol (1)

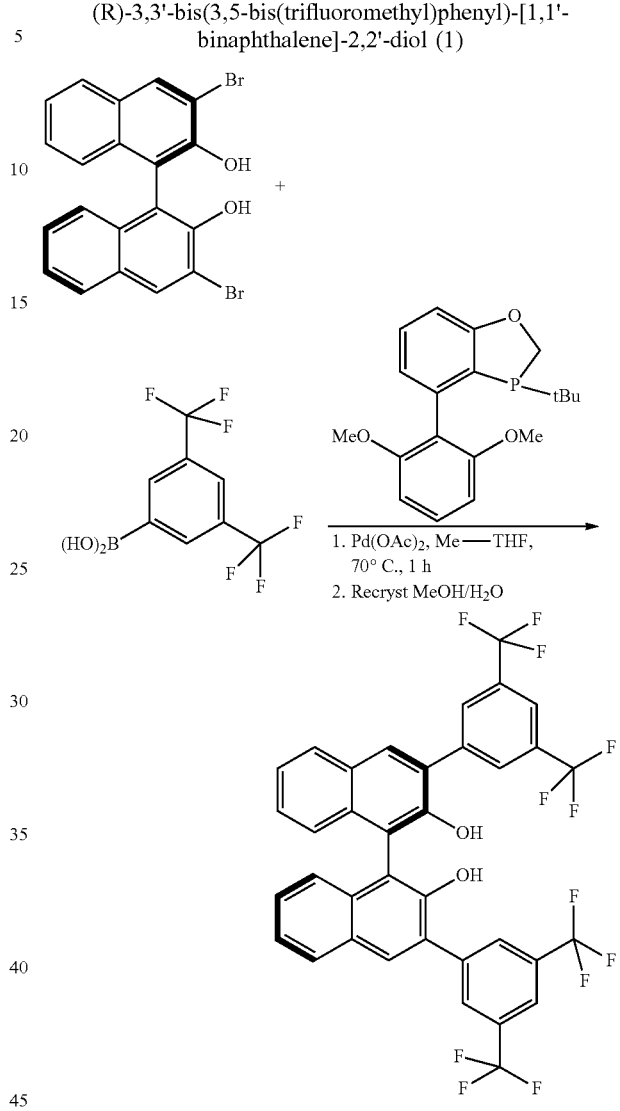

Charge (R)-di-bromo-BINOL (6.0 g, 12.5 mmol), (3,5-bis(trifluoromethyl)phenyl)boronic acid (8.067 g, 31.3 mmol), Na$_2$CO$_3$ (3.98 g, 38.0 mmol), MeTHF (45 mL) and H$_2$O (15 mL) to a 250-mL reactor. Purge the mixture with N$_2$ for 20 min, then add Pd(OAc)$_2$ (14.6 mg, 0.065 mmol) and racemic 4-(2,6-dimethoxyphenyl)-3-(1,1-dimethylethyl)-2,3-dihydro-1,3-benzoxaphosphole (*Angew Chem Int Ed* 49 (2010), 5879-83, 24.7 mg, 0.075 mmol). Heat the reaction to 70° C. for 2 h, cool down to 20° C. then add 15 mL H$_2$O. Separate the layers then wash the organic fraction with water (20 mL). Treat the organic fraction with Darco 60 (0.3 h), filter then solvent switch to MeOH (45 mL). Heat the solution to 60° C. then crystallize the product by slow addition of water (45 mL). Cool down to 20° C., filter the product then dry under reduced pressure at 70° C. for 20 h.

Yield: 8.57 g (91%)
ee>99.5% (Method O)
$^1$H NMR (400 MHz, CDCl$_3$): δ 8.23 (s, 4H), 8.11 (s, 2H), 7.99 (d, J=8.2 Hz, 2H), 7.91 (s, 2H), 7.47 (dt, J=7.2, 1.0 Hz, 2H), 7.41 (dt, J=8.0, 1.4 Hz, 2H), 7.22 (d, J=8.5 Hz, 2H), 5.46 (s, 2H)

(R)-3,3'-bis[3,5-bis(trifluormethyl)phenyl]-1,1'-binaphthyl-2,2'-dihydrogenphosphate

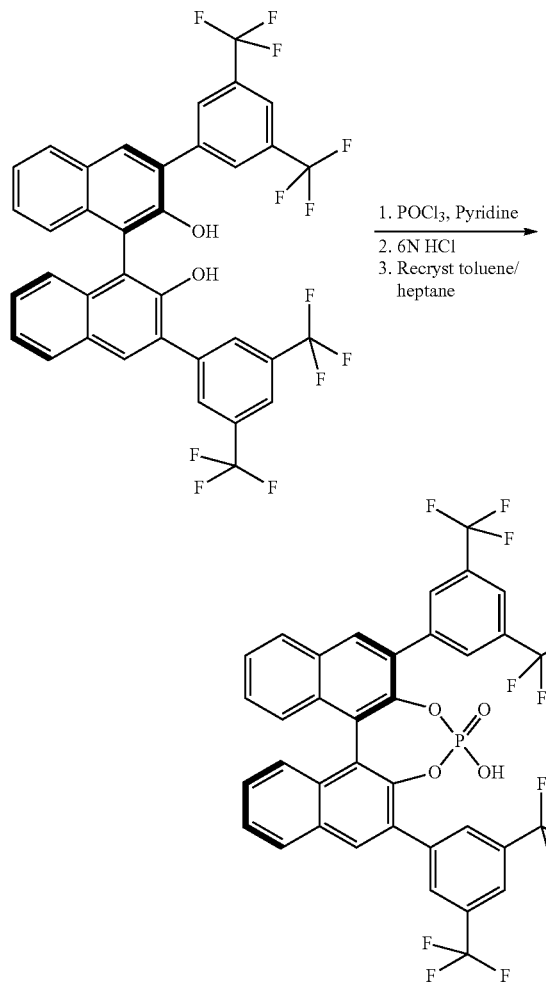

Charge (R)-3,3'-bis(3,5-bis(trifluoromethyl)phenyl)-[1,1'-binaphthalene]-2,2'-diol (1) (5.5 g, 7.40 mmol), and pyridine (15 mL) to a 250-mL reactor. Slowly add a solution of phosphorus oxychloride (1.71 g, 11.152 mmol) in pyridine (7.5 mL while maintaining the reaction temperature below 30° C. Stir the reaction mixture at 80° C. for 1.5 h, cool down to 40° C. then add water (7.5 mL) followed after 10 min by addition of HCl (6N) solution (37 mL). Heat the reaction to 100° C. for 1 h, cool down to 20° C. then filter the solids. Wash the solids with water (15 mL) then return them to the reactor. Add toluene (60 mL) and HCl (6N) (15 mL). Heat the mixture to 40° C. for 20 min then separate the aqueous fraction. Wash the organic fraction at 30-40° C. with 2×15 mL 6N HCl then with water (20 mL). Distill toluene to reach 17 mL of product solution, Heat to 60° C. then add heptane (60 mL) to crystallize the product. Cool down to 20° C. then filter, wash with heptane then dry under reduced pressure at 70° C. for 20 h.

Yield: 3.82 g (66.4%)
ee>99.5% (Method P)
$^1$H NMR (400 MHz, CDCl$_3$): δ 8.01 (m, 8H), 7.57 (m, 4H), 7.42 (m, 4H), 6.28 (s, 1H).
HPLC Methods Method: A
Device-Description Agilent 1200 with DA-Detector
Column: Halo-5, 3 × 50 mm, 5 μm
Column Supplier: Waters

| Gradient/Solvent Time [min] | % Sol [0.2% KH$_2$PO$_4$, pH = 3] | % Sol [Acetonitrile] | Flow [ml/min] | Temp [° C.] |
|---|---|---|---|---|
| 0.00 | 80 | 20 | 2.3 | 50 |
| 4.00 | 20 | 80 | 2.3 | 50 |

Method: B
Device-Description Agilent 1100 with DAD
Column Chiralpak AD-H
Column Dimension 150 * 4.6 mm
Particle Size 5 μm

| Solvent Gradient time [min] | % Sol [0.2% KH$_2$PO$_4$, pH = 3] | % Sol [Acetonitrile] | Flow [ml/min] | Temp [° C.] | Backpressure [bar] |
|---|---|---|---|---|---|
| 0.00 | 90 | 10 | 1.0 | 25 | |
| 10.00 | 90 | 10 | 1.0 | 25 | |

Method: C
Device-Description Agilent 1200 with DA- and MS-Detector
Column: Sunfire, 3 × 30 mm, 2.5 μm
Column Supplier: Waters

| Gradient/Solvent Time [min] | % Sol [H2O, 0.1% TFA] | % Sol [Acetonitrile] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: D
Device-Description Agilent 1260 SFC with DAD and MS
Column Daicel Chiralpak ® IC
Column Dimension 4.6 × 250 mm
Particle Size 5 μm

| Solvent Gradient time [min] | % Sol [scCO$_2$] | % Sol [MeOH, 20 mM ammonia] | Flow [ml/min] | Temp [° C.] | Backpressure [bar] |
|---|---|---|---|---|---|
| 0.00 | 70 | 30 | 4 | 40 | 150 |
| 10.00 | 70 | 30 | 4 | 40 | 150 |

Method: E
Device-Description Waters Acquity with DA- and MS-Detector
Column: Xbridge BEH C18, 2.1 × 30 mm, 1.7 μm
Column Supplier: Waters

| Gradient/Solvent Time [min] | % Sol [H2O, 0.1% NH3] | % Sol [Acetonitrile] | Flow [ml/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method F
Device-Description Agilent 1260 SFC with DAD and MS
Column Daicel Chiralpak ® IC
Column Dimension 4.6 × 250 mm
Particle Size 5 μm

| Solvent Gradient time [min] | % Sol [scCO$_2$] | % Sol [MeOH, 20 mM ammonia] | Flow [ml/min] | Temp [° C.] | Backpressure [bar] |
|---|---|---|---|---|---|
| 0.00 | 70 | 30 | 4 | 40 | 150 |
| 10.00 | 70 | 30 | 4 | 40 | 150 |

Method Name: G
Device-Description Waters Alliance with DA- and MS-Detector
Column: XBridge C18, 4.6 × 30 mm, 3.5 μm
Column Supplier: Waters

| Gradient/Solvent Time [min] | % Sol [H2O, 0.1% NH3] | % Sol [ACN] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method H
Device-Description Agilent 1260 SFC with DAD and MS
Column Daicel Chiralpak ® IA
Column Dimension 4.6 × 250 mm
Particle Size 5 μm

| Solvent Gradient time [min] | % Sol [scCO$_2$] | % Sol [MeOH, 20 mM ammonia] | Flow [ml/min] | Temp [° C.] | Backpressure [bar] |
|---|---|---|---|---|---|
| 0.00 | 80 | 20 | 4 | 40 | 150 |
| 10.00 | 80 | 20 | 4 | 40 | 150 |

Method: I
Device-Description Agilent 1260 SFC with DAD
Column Daicel Chiralpak ®-IA
Column Dimension 4.6 × 250 mm
Particle Size 5 μm

| Solvent Gradient time [min] | % Sol [scCO$_2$] | % Sol [MeOH] | Flow [ml/min] | Temp [° C.] | Backpressure [bar] |
|---|---|---|---|---|---|
| 0.00 | 90 | 10 | 3 | 37.5 | 100 |
| 6.00 | 90 | 10 | 3 | 37.5 | 100 |

Method: K
Device-Description Agilent 1260 SFC with DAD
Column Daicel Chiralpak ®-IA
Column Dimension 4.6 × 250 mm
Particle Size 3 μm

| Solvent Gradient time [min] | % Sol [scCO$_2$] | % Sol [MeOH] | Flow [ml/min] | Temp [° C.] | Backpressure [bar] |
|---|---|---|---|---|---|
| 0.00 | 90 | 10 | 3.5 | 37.5 | 120 |
| 6.00 | 90 | 10 | 3.5 | 37.5 | 120 |

Method: L
Device-Description Agilent 1260 SFC with DAD
Column Daicel Chiralpak ®-IA
Column Dimension 4.6 × 250 mm
Particle Size 3 μm

| Solvent Gradient time [min] | % Sol [scCO$_2$] | % Sol [MeOH] | Flow [ml/min] | Temp [° C.] | Backpressure [bar] |
|---|---|---|---|---|---|
| 0.00 | 95 | 5 | 3.5 | 37.5 | 120 |
| 10.00 | 95 | 5 | 3.5 | 37.5 | 120 |

Method: M
Device-Description Agilent 1260 SFC with DAD
Column Lux-Cellulose-1
Column Dimension 4.6 × 250 mm
Particle Size 3 μm

| Solvent Gradient time [min] | % Sol [scCO$_2$] | % Sol [MeOH] | Flow [ml/min] | Temp [° C.] | Backpressure [bar] |
|---|---|---|---|---|---|
| 0.00 | 80 | 20 | 3.0 | 37.5 | 100 |
| 5.00 | 80 | 20 | 3.0 | 37.5 | 100 |

Method: N
Device-Description Agilent 1100/1200
Column Sunfire C18
Column Dimension 3.0 × 30 mm
Particle Size 2.5 μm

| Solvent Gradient time [min] | % Sol [H$_2$O, 0.2% HCOOH] | % Sol [Acetonitrile] | Flow [ml/min] | Temp [° C.] | Backpressure [bar] |
|---|---|---|---|---|---|
| 0.10 | 97 | 3 | 2.3 | 50 | 400 |
| 1.40 | 0 | 100 | 2.3 | 50 | 400 |
| 1.60 | 0 | 100 | 2.3 | 50 | 400 |
| 1.80 | 97 | 3 | 2.3 | 50 | 400 |

Method: O
Device-Description Agilent 1100/1200
Column Chiralpak AD-3
Column Dimension 4.6 × 150 mm
Particle Size 3 μm

| Solvent Gradient time [min] | % Sol [Heptane] | % Sol [Isopropanol] | Flow [ml/min] | Temp [° C.] | Backpressure [bar] |
|---|---|---|---|---|---|
| 0 | 99.5 | 0.5 | 1.0 | 25 | 150 |
| 10 | 99.5 | 0.5 | 1.0 | 25 | 150 |

Method: P
Device-Description Agilent 1100/1200
Column (R,R) Whelk-01; Cat# 1-780223-300
Column Dimension 4.6 × 250 mm
Particle Size 3.5 μm

| Solvent Gradient time [min] | % Sol [Heptane] | % Sol [Ethanol 0.2% Diethyl amine] | Flow [ml/min] | Temp [° C.] | Backpressure [bar] |
|---|---|---|---|---|---|
| 0.0 | 90 | 10 | 1.3 | 25 | 150 |
| 9.0 | 90 | 10 | 1.3 | 25 | 150 |

The invention claimed is:
1. A method for the preparation of a compound of formula (IV),

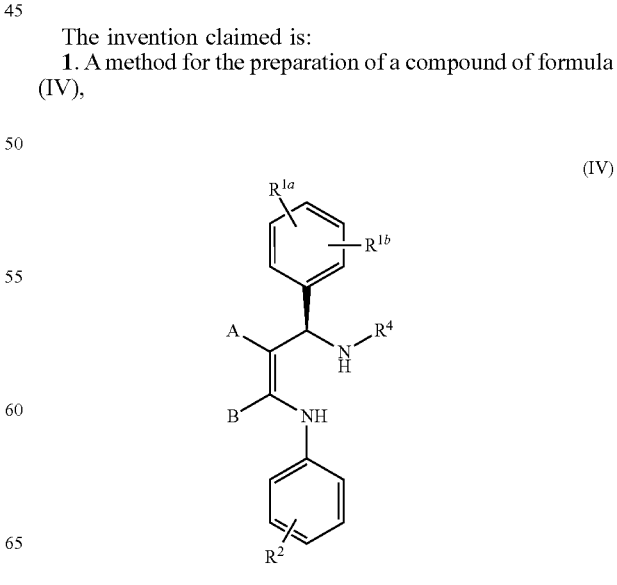

wherein
R$^{1a}$ is NC—;
R$^{1b}$ is H, CH$_3$S—, Br, CH$_3$SO$_2$—;
A is NC—;
B is CH$_3$;
or A and B together with the carbon atoms to which they are attached form a ring selected from the group consisting of cyclopentenone, cyclohexenone and furanone;
R$^2$ is F$_3$C—;
R$^4$ is

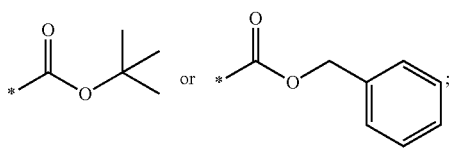

characterised in that the method comprises step (C), where step (C) is the stereoselective reaction of a compound of formula (I)

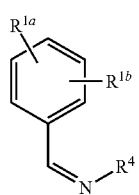

with a compound of formula (III)

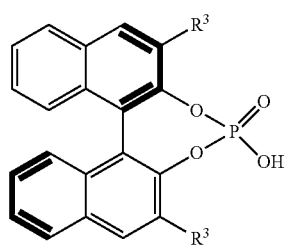

wherein A, B, R$^{1a}$, R$^{1b}$, R$^2$ and R$^4$ have the meanings as defined above;
in the presence of an organo-catalyst of formula (X)

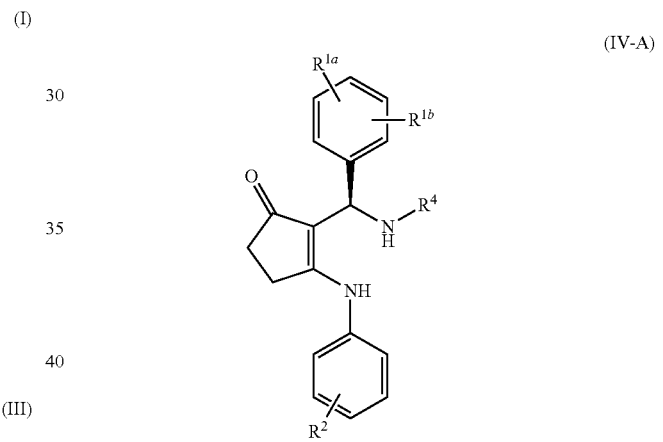

wherein
R$^3$ is selected from the group consisting of

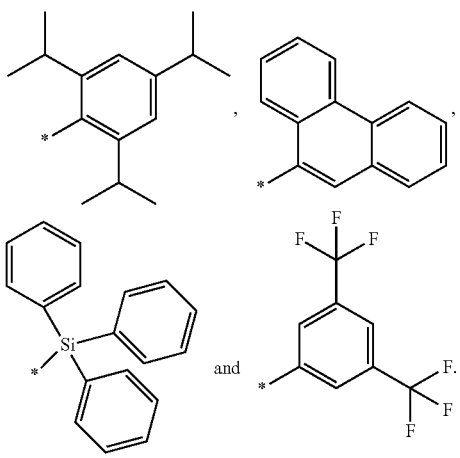

2. The method according to claim 1, for the preparation of compounds of formula (IV-A)

wherein a compound of formula (I-A)

is reacted with a compound of formula (III) in the presence of an organo-catalyst of formula (X);
wherein R$^{1a}$, R$^{1b}$, R$^2$ and R$^4$ have the meanings as defined above.

3. The method according to claim 1, wherein R$^3$ of organo-catalyst of formula (X) is

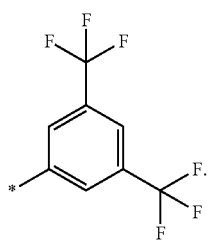 [SMILES: *c1cc(C(F)(F)F)cc(C(F)(F)F)c1]

4. The method according to claim 1, wherein step (C) is carried out at a temperature from 0° C. to −70° C.

5. The method according to claim 1, wherein step (C) is carried out in a solvent selected from the group consisting of ethyl acetate, Me-THF, THF, dichloromethane, isopropyl acetate, n-butyl acetate, toluene and DMF.

6. The method according to claim 1, wherein step (C) is carried out using from 0.3 mol % to 10 mol % of the organo-catalyst of formula (X).

7. The method according to claim 1, wherein step (C) is carried out using from 1.0 to 1.5 molar equivalents of the compound of formula (I).

8. The method according to claim 1, wherein step (C) is carried out using 1.0 molar equivalents of compound of formula (III).

9. A method for the preparation of organo-catalyst of formula (X),

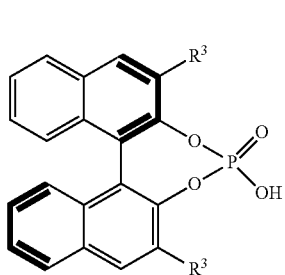

(X)

wherein R³ is

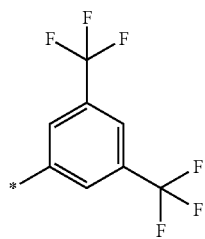 [SMILES: *c1cc(C(F)(F)F)cc(C(F)(F)F)c1]

characterised in that the method comprises a Suzuki-Miyaura coupling of unprotected 3,3'-dibromo-1,1-bi-2-napthol with 3,5-bis-(trifluoromethyl)phenyl boronic acid in the presence of palladium diacetate and a ligand of formula (Y)

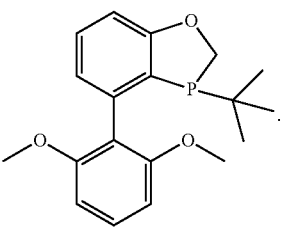

(Y)

* * * * *